US005766871A

United States Patent [19]
Chu et al.

[11] Patent Number: 5,766,871
[45] Date of Patent: Jun. 16, 1998

[54] SCREENING AND CHARACTERIZATION OF GLUTARYL-7-AMINOCEPHALOSPORANIC ACID ACYLASE

[75] Inventors: Wen-Shen Chu, Hsin-Chu; Yun-Huey Lee, Kao-Hsiung; Ming-Chu Chen, Taipei; Li-Lin Chen, Hsin-Chu; Chiou-Yen Wen, Miao-Li, all of Taiwan

[73] Assignee: Food Industry Research and Development Institute, Hsinchu, Taiwan

[21] Appl. No.: 757,467

[22] Filed: Nov. 27, 1996

[51] Int. Cl.$^6$ .................... C12Q 1/34; G01N 33/52; C12P 21/00; C12N 9/50
[52] U.S. Cl. .................... 435/18; 435/7.4; 435/71.2; 435/228
[58] Field of Search .................... 435/228, 7.4, 18, 435/252.34, 71.2

[56] References Cited

U.S. PATENT DOCUMENTS

| 5,192,678 | 3/1993 | Iwami et al. ............... 435/228 |
| 5,320,948 | 6/1994 | Iwami et al. ............... 435/47 |
| 5,332,663 | 7/1994 | Battistel et al. ............ 435/51 |
| 5,612,210 | 3/1997 | Van Der Goes et al. ...... 435/228 |

FOREIGN PATENT DOCUMENTS

| 0 504 798 A1 | 3/1992 | European Pat. Off. . |
| 61-1522286 | 7/1986 | Japan . |
| 93-08972 | 9/1993 | Rep. of Korea . |
| WO 88/06624 | 9/1988 | WIPO . |

OTHER PUBLICATIONS

Aramori et al., "Isolation of Soil Strains Producing New Cephalosporin Acylases", J. Fermentation and Bioengineering, (1991) 72(4): 227–231.
Binder et al., "Isolation and Characterization of a Pseudomonas Strain Producing Glutaryl–7–Aminocephalosporanic Acid Acylase", Applied and Environmental Microbiology, Oct. (1993), pp. 3321–3326.
Chen et al., "Screening and Characterization of Glutaryl–7–Aminocephalosporanic Acid Acylase from Pseudomonas sp.", Biotechnology Techniques, (1995) 9(12): 859–862.
Deshpande et al., "Molecular biology of β–lactam acylases", World Journal of Microbiology & Biotechnology, (1994) 10: 129–138.
Franzosi et al, "Screening and characterization of microorganisms with glutaryl–7ADCA activity", Appl. Microbiol. Biotechnol. (1995) 43:508–513.

Iizuka et al, "Microbiological Studies on Petroleum and Natural Gas", J. Gen. Appl. Microbiol., (1964) 10(3): 207–221.
Nikolov et al., "Enzymatic transformation of cephalosporin C to 7–amino–cephalosporanic acid", Enzyme Microb. Technol. (1994) 16: 1037–1041.
Nikolov et al., "Enzymatic transformation of cephalosporin C to 7–amino–cephalosporanic acid", Enzyme Microb. Technol. (1994) 16: 1031–1036.
Shibuya et al., "Isolation and Properties of 7β–(4–Carboxybutanamido)cephalosporanic Acid Acylase–producing Bacteria", Agric. Biol. Chem., (1981) 45(7): 1561–1567.
Sudhakaran et al., "Molecular Aspects of Penicillin and Cephalosporin Acylases", Process Biochemistry, (1992) 27: 131–143.
Matsuda, A., Journal of Bacteriology, vol. 169, "Nucleotide sequences of the genes for two distinct cephalosporin acylases from a Pseudomonas strain", pp. 58–21–5826, 1987.
Aramori, I., et al., Journal of Fermentation and Bioengineering, vol. 72, "Cloning nucleotide sequencing of new glutaryl 7–ACA and cephalosporin C acylase genes from Pseudomonas strains", pp. 232–243, 1991.
Meng, G.–Z., Annals of the New York Academy of Sciences, vol. 672, "Improvement of germoplasms of enzyme–producing microbial strains by genetic engineering", pp. 114–117, 1992.
Bouvrette, P., et al., Analytical Biochemistry, vol. 200, "Use of delta–(alpha–aminoadipoyl) chromogenic amides in screening for aminoadipoyl amidohydrolases", pp. 315–320, 1992.
Liu, G., et al., Chinese Journal of Antibiotics, vol. 18, "Selection of a high–yield Gl–7ACA acylase producer, Pseudomonas strain 79u–18", pp. 434–438, 1993.
Binder, R., et al., Applied and Environmental Microbiology, vol. 60, "Biochemical characterization of a glutaryl–7–aminocephalosporanic acid acylase from Pseudomonas strain BL072", pp. 1805–1809, 1994.
Sonawane, V.C., et al., Biotechnology Letters, vol. 18, "Cephalosporin modification: An extracellular glutaryl–7–ACA acylase from Bacillus sp.", pp. 965–968, 1996.

*Primary Examiner*—Robert A. Wax
*Assistant Examiner*—William W. Moore
*Attorney, Agent, or Firm*—Fish & Richardson P.C.

[57] ABSTRACT

A method of screening for a given enzyme in colony-forming cells using a substrate of the enzyme that has low solubility. Use of such a method leads to the discovery of glutaryl-7-aminocephalosporanic acid (GL-7-ACA) acylase of *Pseudomonas nitroreducens*. Also disclosed is a method of obtaining GL-7-ACA acylase from Pseudomonas cells.

15 Claims, No Drawings

SCREENING AND CHARACTERIZATION OF GLUTARYL-7-AMINOCEPHALOSPORANIC ACID ACYLASE

BACKGROUND OF THE INVENTION

7-Aminocephalosporanic acid (7-ACA) is the starting material for industrial production of semisynthetic cephalosporin antibiotics. 7-ACA can be generated from cephalosporin C (Ceph C) by a two-step enzymatic reaction using D-amino acid oxidase and glutaryl-7-aminocephalosporanic acid (GL-7-ACA) acylase.

SUMMARY OF THE INVENTION

The invention features GL-7-ACA acylase of *Pseudomonas nitroreducens* [e.g., the bacteria having the identifying characteristics of the American Type Culture Collection (ATCC) 33634 strain]. The acylase can be either naturally occurring or recombinant. Typically, it is most active at a temperature between 37° C. and 42° C., inclusive; and at a pH between 4.5 and 6.0, inclusive; and it can contain two subunits—$\alpha(35\pm4$ kDa) and $\beta(21\pm2$ kDa). The acylase of the present invention can have a pI value of $5.3\pm0.5$. It can also have a $K_m$ value of $1.58\pm0.2$ mM for glutaryl-desacetoxy-7-aminocephalosporanic acid (GL-7-ADCA) and a $K_m$ value of $6.11\pm0.6$ mM for GL-7-ACA. The $\alpha$ subunit of the present acylase can have an N-terminal sequence of VTLDGGAVAAP (SEQ ID NO:1) or its homologous sequence (e.g., having Valine substituted by Alanine, threonine substituted by serine, and the like), and the $\beta$ subunit, on the other hand, can have an N-terminal sequence of TTHFSIVDKDG (SEQ ID NO:2) or its homologous sequence (e.g., having threonine substituted by serine, isoleucine substituted by leucine, and the like). All of the aforementioned properties of the acylase are determined by methods described in the working examples below or analogous methods.

The invention also features a method of determining whether a cell that can form a colony in a solid culture medium has the activity of a given enzyme. In this method, one can grow the cell in a solid (including semi-solid) culture medium which contains a substrate of the enzyme. The substrate should have a low solubility so that it confers a turbidity or opaqueness to the medium. Upon the action of the enzyme, the substrate should be converted to a soluble product or products. Thus, if a colony formed (inside the medium or on surface of the medium) from a seeded cell contains the enzyme, there will be a clearer zone around it due to decreased turbidity of the medium. The cell which can be used in the above-described method may be a microorganism or derived from a higher organism (e.g., an insect, an amphibian, or a mammal). A microorganism, as used herein, can be, but is not limited to, a bacterium, or a fungus (e.g., a yeast).

The above-described method can be used to screen for the activity of glutaryl-7-aminocephalosporanic acid acylase in microorganisms. In this case, a substrate compound that can be used is glutaryl-naphthylamide or its derivative. A derivative of glutaryl-naphthylamide is any compound that is similar to glutaryl-naphthylamide in structure, has low solubility in a culture medium, and is the substrate of GL-7-ACA acylase. The microorganism that can be used to screen for the acylase can be of the genus Pseudomonas, Xanthomonas, or Bacillus, or of any other suitable genus.

Within the scope of the invention is also a method of obtaining a glutaryl-7-aminocephalosporanic acid acylase from Pseudomonas cells. The Pseudomonas cells can, for instance, be from ATCC 33634. In this method, the Pseudomonas cells are cultured in a medium containing 0–5 g/l meat extract, 0–10 g/l peptone, 1–3 g/l yeast extract, 0–1 g/l glutaric acid, and 2–10 g/l sodium chloride. Preferably, the medium contains 10 g/l peptone, 2 g/l yeast extract, and 5 g/l sodium chloride, and more preferably, the medium does not contain any meat extract or glutaric acid. Meat extract, peptone, and yeast extract can be obtained from Difco, Detroit, Mich., or be substituted by any composition deemed equivalent by one of ordinary skill in the art.

Other features or advantages of the present invention will be apparent from the following detailed description and from the appending claims.

DETAILED DESCRIPTION OF THE INVENTION

Characterization of the present acylase, e.g., purification, peptide sequencing, measurements of the optimal temperature and pH, pI, and $K_m$ for a substrate can be performed by methods well known in the art and is illustrated below. All reagents used herein are of analytical grade unless described individually. To screen cells (eukaryotic or prokaryotic) for the activity of a given enzyme, the cells are separated and individual cells are grown in a solid culture medium to form distinct colonies. The solid culture medium contains a substrate of the enzyme, and the substrate has low solubility so that it contributes to the turbidity or opaqueness of the culture medium. Such a substrate can be obtained by modifying a known soluble substrate of the enzyme, e.g., introducing to the substrate substituent groups that are known in the art to decrease aqueous solubility of a compound. A clearer zone surrounding a colony indicates that the cells of the colony contain the enzyme.

Without further elaboration, it is believed that one skilled in the art can, based on the description herein, utilize the present invention to its fullest extent. The following specific examples are, therefore, to be construed as merely illustrative, and not limitative of the remainder of the disclosure in any way whatsoever. All citations are incorporated by reference. By "one skilled in the art" is meant a person of ordinary skill in the art as judged during the period from the filing date of this application to the expiracy of any patent issuing from it.

Screening of GL-7-ACA acylase-producing strains of the genus Pseudomonas

Three hundred strains of Pseudomonas sp. from culture collection and local isolates of Taiwan were screened for GL-7-ACA acylase activity using three methods. First, they were tested for their abilities to use GL-7-ADCA (glutaryl-desacetoxy-7-aminocephalosporanic acid) as the sole carbon and nitrogen source for growth. Second, strains which grew well under the first condition were screened for their activities against glutaryl-naphthylamide, an analogue of GL-7-ACA with low solubility, on nutrient agar plates. Strains active against glutaryl-naphthylamide could form clear zones in the agar, due to the degradation of glutaryl-naphthylamide. Finally, positive strains from the second screening were tested for GL-7-ACA acylase activities using p-dimethylaminobenzaldehyde (p-DBA) colorimetric assay (Shibuya et al., *Agric. Biol. Chem.* 45: 1561–1567, 1981).

Specifically, the 300 Pseudomonas strains were spotted on PM plates [0.15% $(NH_4)_2HPO_4$, 0.1% $KH_2PO_4$, 0.05% $MgSO_4 \cdot 7H_2O$, 0.001% $FeCl_3 \cdot 6H_2O$, 0.001% $MnCl_2 \cdot 4H_2O$, 0.001% NaCl, 1.5% agar] containing 10 mM GL-7-ADCA (prepared as described by Shibuya et al., *Agric. Microbiol. Technol.* 45: 1561–1567, 1981) and incubated at 30° C. for 2–3 days. Well grown colonies were transferred onto nutrient agar (NA; agar: Difco, Detroit, Mich.) plates containing 0.2% glutaryl-naphthylamide (prepared as described by Shibuya et al., *Agric. Microbiol. Technol.* 45: 1561–1567, 1981) and incubated at 30° C. for 2 days.

Colonies forming clear zones were cultivated in Nutrient Broth (Difco, Detroit, Mich.) and tested for GL-7-ACA acylase activity as described by Shibuya et al. (*Agric. Biol. Chem.* 45: 1561–1567, 1981). The whole-cell suspension of ATCC 33634 in 100 mM acetate buffer (pH 5.0) was used as the acylase source. One unit of the acylase activity was defined as the amount of enzyme that liberates 1 μmole of 7-ADCA per min.

Three positive isolates were so identified, and the results were confirmed by use of HPLC, as described by Binder et al. (*Appl. Environ. Microbiol.* 59: 3321–3326, 1993). A Nova Pack C-18 column (Waters) was used, and the mobile phase was 20 mM ammonium acetate (pH 4.8) containing 3% methanol for GL-7-ADCA and 7-ADCA (Fujii et al., *Process Chem.* 11: 21, 1976), or 10 % methanol for GL-7-ACA and 7-ACA. The retention times for GL-7-ACA, 7-ACA, GL-7-ADCA and 7-ADCA at a flow rate of 1 ml/min were 4.256, 1.630, 7.063 and 1.621 min, respectively.

Two of the three identified positive isolates were *Xanthomonas maltophilia*. The third one, which was *P. nitroreducens* ATCC 33634, had the highest GL-7-ACA acylase activity, and thus was used for further studies.

Cultivation of ATCC 33634

To obtain the optimal medium for *P. nitroreducens* ATCC 33634 cultivation, various media were tested according to the report of Nikolov and Danielsson (*Enzyme Microbiol. Technol.* 16: 1031–1036, 1994) (Table 1). The cultivation was carried out in 500 ml flasks containing 100 ml of media (Table 1) at 30° C. and 150 rpm for 24 hr. All media were adjusted to pH 7.5 before autoclaving. Yeast extract, casein, peptone, and meat extract were purchased from Difco Laboratories Inc. (Detroit, Mich.).

TABLE 1

Effect of composition of media on the production of GL-7-ACA acylase in *P. nitroreducens* ATCC 33634

| Ingredient | Meat extract medium (g/l) | | | | Casein medium (g/l) | Peptone medium (g/l) |
| --- | --- | --- | --- | --- | --- | --- |
| | I | II | III | IV | | |
| Meat extract | 5 | — | 5 | 5 | — | — |
| Casein | — | — | — | — | 20 | — |
| Peptone | 10 | 10 | — | 10 | — | 10 |
| Corn-steep liquor* | — | — | — | — | — | 10 |
| Sodium glutamate | — | — | — | — | 5 | — |
| Yeast extract | 2 | 2 | 2 | 2 | 2 | — |
| Glutaric acid | 0.5 | — | — | — | 0.5 | 0.5 |
| Sodium chloride | 5 | 5 | 5 | 5 | — | — |
| Relative activity | 90.33 | 107.7 | 98.98 | 100 | 4.56 | 63.36 |

*Concentration in ml/l

The medium in which *P. nitroreducens* ATCC 33634 grew most rapidly was the casein medium. However, little GL-7-ACA acylase activity was detected under this condition. The meat extract medium II was the best medium for the expression of GL-7-ACA acylase activity in ATCC 33634. The highest level of GL-7-ACA activity appeared at 30 hr of cultivation. No acylase activity was detected in the centrifuged supernatants of the cultural broths, suggesting that the acylase was localized inside the cells. Glutaric acid, the reported inducer for GL-7-ACA acylases (Shibuya et al., *Agric. Biol. Chem.* 45: 1561–1567, 1981; Nikolov and Danielsson, *Enzyme Microbiol. Technol.* 16: 1031–1036, 1994) did not induce the GL-7-ACA acylase activity in ATCC 33634. On the contrary, it inhibited the acylase activity at a concentration as low as 0.02%, and at 0.12%, inhibited up to 50% of the enzyme activity.

Substrate specificity of GL-7-ACA acylase

Cells of ATCC 33634 were used to convert GL-7-ACA and related compounds (Table 2). GL-7-ACA, GL-7-ADCA, and succinyl-7-ACA were prepared according to the method of Shibuya et al. (*Agric. Biol. Chem.* 45: 1561–1567, 1981).

GL-7-ADCA was a better substrate for ATCC 33634 acylase than was GL-7-ACA, nearly three times more activity being detected. No activity was detected against Ceph C and succinyl-7-ACA. The enzyme appeared to belong to the GL-7-ACA acylase II family according to the classification scheme of Deshpande et al., *World J. Microbiol. Biotechnol.* 10: 129–138, 1994. Acylases of *Bacillus laterasporus* (Aramori et al., *J. Ferment. Bioeng.* 72: 227–231, 1991), *Pseudomonas* sp. GK16 (Ichikawa et al., *Agric. Biol. Chem.* 45: 2231–2236, 1981), and *Pseudomonas* sp. SE83-1 (Matsuda et al., *J. Bacteriol.* 169: 5815–5820, 1987) are of the same family.

The $K_m$ values of the present acylase for GL-7-ADCA and GL-7-ACA, as determined by well known techniques, are 1.58 mM and 6.11 mM, respectively.

TABLE 2

Substrate profile of GL-7-ACA acylase of *P. nitroreducens* ATCC 33634.

| substrate | relative activity* |
| --- | --- |
| GL-7ADCA | 294 |
| GL-7ACA | 100 |
| Succinyl-7ACA | not detected |
| Ceph C | not detected |

*The relative GL-7-ACA acylase activity was presented as percentage relative to the activity for GL-7-ACA. Whole cells of ATCC 33634 were incubated with 0.2 g/l of GL-7-ACA, GL-7-ADCA, succinyl 7-ACA, or Ceph C at 37° C. for 3 hr.

Purification of GL-7-ACA Acylase

Crude acylase preparation was obtained by treating the *P. nitroreducens* ATCC 33634 cells with supersonic sound. The similarity in acylase activity between the preparation and intact cells suggested that the acylase be localized in the periplasmic space of the cells. Thus, to obtain an acylase preparation that is relatively free of other cellular proteins, osmotic shock (Neu and Heppel, *J. Biol. Chem.* 240: 3685–3692, 1965) was applied to the cells and the acylase was subsequently extracted without breaking the plasma membrane (Table 3).

Specifically, 36 g (wet weight) of bacterial cells were suspended in 1,200 ml of an ice cold solution that contained 50 mM sodium acetate (pH 5.0), 20% sucrose, and 1 mM EDTA. The cell suspension was incubated at room temperature for 10 min, and subsequently centrifuged to harvest the cells. The cells were then resuspended in 1,200 ml of iced water and incubated for 10 min. The cell suspension was centrifuged to remove the bacterial cells; and the supernatant, which contained the eluted periplasmic fraction of the cells, was collected as the crude acylase preparation.

TABLE 3

Purification of acylase from *Pseudomonas nitroreducens*.

| Step | Total activity (units) | Protein (mg) | Specific Activity (U/mg) | Purification fold | Yield (%) |
| --- | --- | --- | --- | --- | --- |
| Cell suspension | 73.9 | 2880 | 0.0256 | 1 | 100 |
| Osmotic shock | 24.6 | 103 | 0.2392 | 9.34 | 33.3 |
| CM-Sepharose | 19.4 | 13 | 1.4923 | 58.29 | 26.3 |

To obtain highly purified preparation of the acylase, the above described crude preparation (1,200 ml) was applied to a carboxymethyl (CM) -Sephalose column that was pre-equilibrated with Buffer 1 (50 mM sodium acetate, pH 5.0). After washing the column with Buffer 1, the acylase protein was eluted with 800 ml of Buffer 2 (50 mM sodium acetate, pH 5.0; 0.1 M sodium chloride) at a flow rate of 60 ml/hr.

The active fractions, 150 ml in total, was dialyzed against Buffer 1 to remove sodium chloride, and then filtered, condensed by Amicon YM 10 to a final volume of 10 ml.

The use of osmotic shock to extract GL-7-ACA acylase from *P. nitroreducens* greatly improved the acylase concentration in the preparation, and made it feasible to use one-step CM column chromatography to obtain highly purified preparation of the acylase. Thus this method will be of tremendous use for purifying the enzyme on a large scale.

BIOCHEMICAL ANALYSES

Molecular Weight

The molecular weight of the present acylase was approximately 56 kDa, as determined by FPLC Superdex G75 (Pharmacia Fine Chemicals, Uppsala, Sweden) chromatography. The protein markers used were bovine serum albumin (66 kDa), ovalbumin (45 kDa), chymotrypsinogen (25 kDa), and cytochrome C (14 kDa).

SDS-PAGE (sodium dodecyl sulphate-polyacrylamide gel electrophoresis; Sambrook et al., Molecular Cloning, A laboratory Manual, 2nd Edition, Cold Spring Harbor Laboratory, Cold Spring Harbor, N.Y., 1989) revealed that the acylase consists of 2 different subunits, the molecular weights of which are 35 kDa and 21 kDa, respectively. Proteins used as markers were phosphorylase D (197 kDa), bovine serum albumin (66 kDa), ovalbumin (45 kDa), carbonic anhydrase (31 kDa), soybean trypsin inhibitor (21.5 kDa), and lysozyme (14.4 kDa).

The molecular composition of the present acylase, as described above, is clearly distinguishable from that of the previously known GL-7-ACA acylases. The prior acylase that most resembles the present one in molecular composition is acylase I of Pseudomonas sp. SE83, which consists of two subunits with respective sizes of 38 kDa and 20 kDa (Matsuda et al., J. Bacteriol. 169: 5821–5826, 1987).

The pI value of the present acylase is 5.3, as determined by well known techniques.

N-Terminal Sequences

The α and β subunits of the present acylase were purified by use of SDS-PAGE, and then transferred onto poly (vinylidene difluoride) membrane (Pharmacia) for N-terminal sequencing, using techniques well known in the art. The N-termini of the α and β subunits are VTLDG-GAVAAP (SEQ ID NO: 1 ) and TTHFSIVDKDG (SEQ ID NO: 2), respectively. Both subunits are distinguishable from those of all other Pseudomonas acylases with respect to N-terminal composition. The β subunit of the present enzyme is the most homologous to γ-glutamyltranspeptidase of *E. coli*.

Inhibitors

It has been reported that the activity of GL-7-ACA acylases can be inhibited by their own products, e.g., 7-ACA and glutaric acid. Thus, the inhibitory effects of various compounds on the present acylase were tested (Table 4). The compounds were 7-ACA, glutaric acid, glutamate, succinyl-7-ACA, and Ceph C, all of which were used at 20 mM. As shown in Table 6, 7-ACA and glutamate had the strongest inhibitory effects on the present acylase. The $K_i$ value of the glutaric acid for the present acylase is 0.88.

TABLE 4

| Effect of various inhibitor on the acylase activity | |
|---|---|
| Inhibitor (20 MM) | Relative activity (%) |
| Control | 100 |
| 7-ACA | 38.9 |
| Glutaric acid | 73.9 |
| Succinyl-7ACA | 66.7 |
| Ceph C | 72.2 |
| Glutamate | <1 |

Effects of pH and temperature

To determine pH and temperature optima, GL-7-ACA acylase activity was analyzed at pH's ranging from 4.0 to 10.0 and at temperatures ranging from 25° to 50° C. The enzyme was active over a narrow pH range of 4.5–6.0 with an optimum at pH 5.0. This result is quite different from that of previous studies where the optimal pH's for acylases were higher than 6.0 (Aramori et al., *J. Ferment. Bioeng.* 72: 227–231, 1991; Ichikawa et al., *Agric. Biol. Chem.* 45: 2231–2236, 1981). The optimal temperature for GL-7-ACA acylase activity of ATCC 33634 was shown to be 42° C., and the enzyme was active at any temperature ranging from 37° to 42° C. The activity decreased sharply above 42° C., with only 31% remaining activity at 48° C. The optimal temperature of the present acylase is similar to that of the J1 acylase (40° C.), but different from those of the A14 (48° C.) and N176 (45°–50° C.) acylases (Aramori et al., *J. Ferment. Bioeng.* 72: 227–231, 1991).

Other Embodiments

The above description of the preferred embodiments are meant to illustrate, but not to limit, the methods and compositions of the present invention. Any modifications of the above described embodiments that are obvious to one of ordinary skill in the art are within the scope and spirit of the invention.

What is claimed is:

1. An isolated glutaryl-7-aminocephalosporanic acid acylase of *Pseudomonas nitroreducens*.

2. The acylase of claim 1, wherein said *Pseudomonas nitroreducens* has the identifying characteristics of the American Type Culture Collection 33634 strain.

3. The acylase of claim 1, wherein said acylase is most active at a temperature between 37° C. and 42° C., inclusive;

most active at a pH between 4.5 and 6.0, inclusive; and includes an α subunit and β subunit, the molecular weights of said α and β subunits being 35±4 kDa and 21±2 kDa, respectively.

4. The acylase of claim 3, wherein said acylase has a pI value of 5.3±0.5.

5. The acylase of claim 3, wherein said acylase has a $K_m$ value of 1.58±0.2 mM for glutaryl-desacetoxy-7-aminocephalosporanic acid, and 6.11±0.6 mM for glutaryl-7-aminocephalosporanic acid.

6. The acylase of claim 1, wherein the acylase comprises an α subunit and a β subunit, the N-terminal amino acid sequence of the α subunit including VTLDGGAVAAP (SEQ ID NO:1), and the N-terminal amino acid sequence of the β subunit including TTHFSIVDKDG (SEQ ID NO:2).

7. A method of obtaining a glutaryl-7-aminocephalosporanic acid acylase from *Pseudomonas nitroreducens*, said method comprising:

culturing a *Pseudomonas nitroreducens* bacterium having the identifying characteristics of the American Type Culture Collection 33634 strain in a medium containing 0–5 g/l meat extract, 0–10 g/l peptone, 1–3 g/l yeast extract, 0–1 g/l glutaric acid, and 2–10 g/l sodium chloride; and preparing said acylase from the bacterial culture thus obtained.

8. A method of determining whether a microorganism produces glutaryl-7-aminocephalosporanic acid acylase, said method comprising:

growing said microorganism in a solid medium to form a colony, wherein said medium contains a substrate of said acylase which substrate has low solubility and thereby renders said medium opaque, said substrate being glutaryl-naphthylamide, or a derivative thereof; and detecting a clearer zone around said colony, said clearer zone being formed due to the conversion of said substrate by said acylase to a soluble product;

wherein the presence of said clearer zone indicates the production of said acylase by said microorganism.

9. The method of claim 8, wherein said microorganism is of the genus Pseudomonas.

10. The method of claim 8, wherein said microorganism is of the genus Bacillus.

11. The method of claim 8, wherein said microorganism is of the genus Xanthomonas.

12. The method of claim 8, wherein said substrate is glutaryl-napthylamide.

13. The method of claim 10, wherein said microorganism is of the genus Pseudomonas.

14. The method of claim 10, wherein said microorganism is of the genus Bacillus.

15. The method of claim 10, wherein said microorganism is of the genus Xanthomonas.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: Not Relevant
        ( D ) TOPOLOGY: linear (i i) MOLECULE TYPE: peptide (v) FRAGMENT TYPE: N-terminal (x i) SEQUENCE DESCRIPTION: SEQ ID NO:1:

Val Thr Leu Asp Gly Gly Ala Val Ala Ala Pro
1               5                   10

(2) INFORMATION FOR SEQ ID NO:2:

(i) SEQUENCE CHARACTERISTICS:
    (A) LENGTH: 11 amino acids
    (B) TYPE: amino acid
    (C) STRANDEDNESS: Not Relevant
    (D) TOPOLOGY: linear (i i) MOLECULE TYPE: peptide (v) FRAGMENT TYPE: N-terminal (x i) SEQUENCE DESCRIPTION: SEQ ID NO:2:

Thr Thr His Phe Ser Ile Val Asp Lys Asp Gly
1               5                   10